US012648894B2

(12) United States Patent
Niwa

(10) Patent No.: US 12,648,894 B2
(45) Date of Patent: Jun. 9, 2026

(54) ZIRCONIA SINTERED BODY CONTAINING NEEDLE-SHAPED METAL OXIDE

(71) Applicant: Kuraray Noritake Dental Inc., Kurashiki (JP)

(72) Inventor: Takahiro Niwa, Aichi (JP)

(73) Assignee: Kuraray Noritake Dental Inc., Kurashiki (JP)

( * ) Notice: Subject to any disclaimer, the term of this patent is extended or adjusted under 35 U.S.C. 154(b) by 495 days.

(21) Appl. No.: 18/268,634

(22) PCT Filed: Dec. 20, 2021

(86) PCT No.: PCT/JP2021/047096
§ 371 (c)(1),
(2) Date: Jun. 21, 2023

(87) PCT Pub. No.: WO2022/138592
PCT Pub. Date: Jun. 30, 2022

(65) Prior Publication Data
US 2024/0033186 A1 Feb. 1, 2024

(30) Foreign Application Priority Data
Dec. 21, 2020 (JP) ................................. 2020-211858

(51) Int. Cl.
*A61K 6/818* (2020.01)
*A61K 6/17* (2020.01)
*A61K 6/824* (2020.01)

(52) U.S. Cl.
CPC ................ *A61K 6/818* (2020.01); *A61K 6/17* (2020.01); *A61K 6/824* (2020.01)

(58) Field of Classification Search
CPC ..... A61K 6/818; A61K 6/824; C01P 2002/60; C01P 2004/10; C04B 2235/3225;
(Continued)

(56) References Cited

U.S. PATENT DOCUMENTS

2008/0118722 A1 5/2008 Shikata et al.
2013/0190164 A1* 7/2013 Ito ....................... C04B 35/4885
423/608
(Continued)

FOREIGN PATENT DOCUMENTS

JP 4514563 B2 7/2010
JP 2012041239 A 3/2012
(Continued)

OTHER PUBLICATIONS https://www.forcegauge.net/en/solution/force/compression_test/
48502 Accessed Dec. 3, 2025 (Year: 2025).*
(Continued)

*Primary Examiner* — Cameron K Miller
(74) *Attorney, Agent, or Firm* — Element IP, PLC

(57) ABSTRACT

The present invention provides a zirconia sintered body that has high strength and is machinable. The present invention relates to a zirconia sintered body comprising zirconia, a stabilizing agent capable of preventing a phase transformation of zirconia, a sintering aid, and a needle-shaped metal oxide. Preferably, the sintering aid comprises niobium pentoxide, and the content of the niobium pentoxide is 5 to 15 parts by mass with respect to total 100 parts by mass of the zirconia and the stabilizing agent. Preferably, the stabilizing agent comprises yttria, and the content of the yttria is 2.5 to 10 mol % with respect to the total number of moles of the zirconia and the yttria.

12 Claims, 1 Drawing Sheet

(58) Field of Classification Search
CPC .... C04B 2235/3232; C04B 2235/3251; C04B 2235/5276; C04B 2235/5436; C04B 2235/3246
See application file for complete search history.

(56) References Cited

U.S. PATENT DOCUMENTS

| | | |
|---|---|---|
| 2015/0183690 A1 | 7/2015 | Kim et al. |
| 2017/0035537 A1 | 2/2017 | Leeson et al. |
| 2017/0327425 A1 | 11/2017 | Gong et al. |

FOREIGN PATENT DOCUMENTS

| | | |
|---|---|---|
| JP | 2015127294 A | 7/2015 |
| JP | 2017077454 A | 4/2017 |
| JP | 2018505829 A | 3/2018 |

OTHER PUBLICATIONS

International Search Report issued Feb. 1, 2022 in PCT/JP2021/047096 (with English translation), 4 pages.
Written Opinion issued Feb. 1, 2022 in PCT/JP2021/047096 (with English translation), 7 pages.
Extended European Search Report issued Oct. 10, 2024, received Oct. 15, 2024, in corresponding European Patent Application No. 21910735.6, 7 pages.

\* cited by examiner

ZIRCONIA SINTERED BODY CONTAINING NEEDLE-SHAPED METAL OXIDE

TECHNICAL FIELD

The present invention relates to a workable zirconia sintered body.

BACKGROUND ART

In recent years, zirconia sintered bodies containing yttria have been used in dental material applications such as dental prostheses. In many cases, such dental prostheses are produced from a zirconia molded body of a desired shape, such as a disc or a prism, prepared by, for example, press forming zirconia particles or molding a slurry or composition containing zirconia particles. The zirconia molded body is then pre-sintered to provide a pre-sintered body (mill blank), which is then sintered after being cut (milled) into a shape of the desired dental prosthesis. A zirconia sintered body excels in strength, and its high strength often makes a zirconia sintered body too hard to be milled. This may cause severe wearing in a dental milling instrument (such as a milling bur), or may even cause the milling machine to automatically shut down in response to increased workload. Against this backdrop, it is common practice to perform sintering after the not fully sintered pre-sintered body (mill blank) is cut (milled) into a shape of the desired dental prosthesis, as noted earlier.

However, this technique is laborious because it involves milling and forming a shape of the desired dental prosthesis after dental molding at the dental clinic, sending the fabricated pre-sintered body of desired shape to a dental laboratory, where the pre-sintered body is sintered into a sintered body with a furnace located in the lab, and sending the sintered body back to the dental clinic, where minor adjustments are made by placing the sintered body in the patient's oral cavity, and checking the bite. That is, it takes considerable time before the dental prosthesis is actually placed on patient's teeth. Given these circumstances, there has been a growing demand for a treatment that can be finished without making the patient visit the dental clinic multiple times, in addition to the demand for reducing the energy cost of dental treatment. In view of these conditions, studies have examined sintered bodies that can be milled while maintaining high strength (Patent Literatures 1 and 2). Patent Literature 1 discloses a zirconia sintered body that does not require a sintering process. The post-sintering particle size is increased to decrease hardness and increase processability.

Patent Literature 2 discloses a shape of a fully sintered zirconia crown preform. The preform can be machined into a crown shape with its reduced processing volume compared to common block shapes, and does not require sintering after processing.

CITATION LIST

Patent Literature

Patent Literature 1: JP 2015-127294 A
Patent Literature 2: JP 2017-077454 A

SUMMARY OF INVENTION

Technical Problem

However, balancing between maintaining excellent strength and enabling milling is a trade-off in the properties of a sintered body after sintering, and achieving these goals simultaneously can be difficult. Indeed, the zirconia sintered body described in Patent Literature 1 has low strength, and fails to satisfy strength and workability at the same time, requiring further improvement. Patent Literature 2 takes the approach to reduce processing itself in the preform, and addresses the challenging task of balancing workability and strength by avoiding this issue. However, the preform has the preset sizes, and cannot accommodate cases exceeding these sizes, for example, such as in the case of a three-unit bridge. That is, the preform involves a selectivity issue concerning shapes of crowns.

It is accordingly an object of the present invention to provide a zirconia sintered body that has high strength and is machinable.

Solution to Problem

The present inventor conducted intensive studies to achieve the foregoing object, and found, for the first time, that a zirconia sintered body satisfying both strength and workability can be obtained by sintering a zirconia molded body comprising zirconia, a stabilizing agent, a sintering aid, and a needle-shaped metal oxide. This has led to another new finding that a zirconia sintered body with high crown-shape selectivity can be obtained. Such zirconia sintered bodies were found to be particularly suited as, for example, dental materials such as dental prostheses. The present inventor completed the present invention after further studies based on these findings.

Specifically, the present invention relates to the following.
[1] A zirconia sintered body comprising zirconia, a stabilizing agent capable of preventing a phase transformation of zirconia, a sintering aid, and a needle-shaped metal oxide.
[2] The zirconia sintered body according to [1], wherein the sintering aid comprises niobium pentoxide, and the content of the niobium pentoxide is 5 to 15 parts by mass with respect to total 100 parts by mass of the zirconia and the stabilizing agent.
[3] The zirconia sintered body according to [1] or [2], wherein the stabilizing agent comprises yttria, and the content of the yttria is 2.5 to 10 mol % with respect to the total number of moles of the zirconia and the yttria.
[4] The zirconia sintered body according to any one of [1] to [3], wherein the needle-shaped metal oxide has an aspect ratio of 1:3 to 1:55 (average fiber diameter:average fiber length).
[5] The zirconia sintered body according to any one of [1] to [4], wherein the content of the needle-shaped metal oxide is more than 0 part by mass and 10 parts or less by mass with respect to total 100 parts by mass of the zirconia and the stabilizing agent.
[6] The zirconia sintered body according to any one of [1] to [5], which has a Vickers hardness of 1,050 HV or less.
[7] The zirconia sintered body according to any one of [1] to [6], which has a fracture toughness value of 5 $MPa \cdot m^{1/2}$ or more.
[8] The zirconia sintered body according to any one of [1] to [7], which has a three-point flexural strength of 500 MPa or more.
[9] The zirconia sintered body according to any one of [1] to [8], which has an average crystal grain size of 1 to 10 μm.
[10] The zirconia sintered body according to any one of [1] to [9], wherein the needle-shaped metal oxide comprises at least one selected from the group consisting of Al, Si, Y, Ti, Zr, and Sn.

[11] The zirconia sintered body according to any one of [1] to [10], wherein the needle-shaped metal oxide is at least one or more selected from the group consisting of Al, Si, Ti, and Sn.

[12] The zirconia sintered body according to any one of [1] to [11], wherein the needle-shaped metal oxide comprises at least one selected from the group consisting of Al and Ti.

[13] The zirconia sintered body according to any one of [1] to [12], wherein the needle-shaped metal oxide comprises $TiO_2$.

Advantageous Effects of Invention

According to the present invention, a zirconia sintered body can be provided that has high strength and is machinable. By making the shape of the machinable zirconia sintered body freely selectable, the present invention can provide a machinable zirconia sintered body having high crown-shape selectivity.

DESCRIPTION OF EMBODIMENTS

Figure 1:
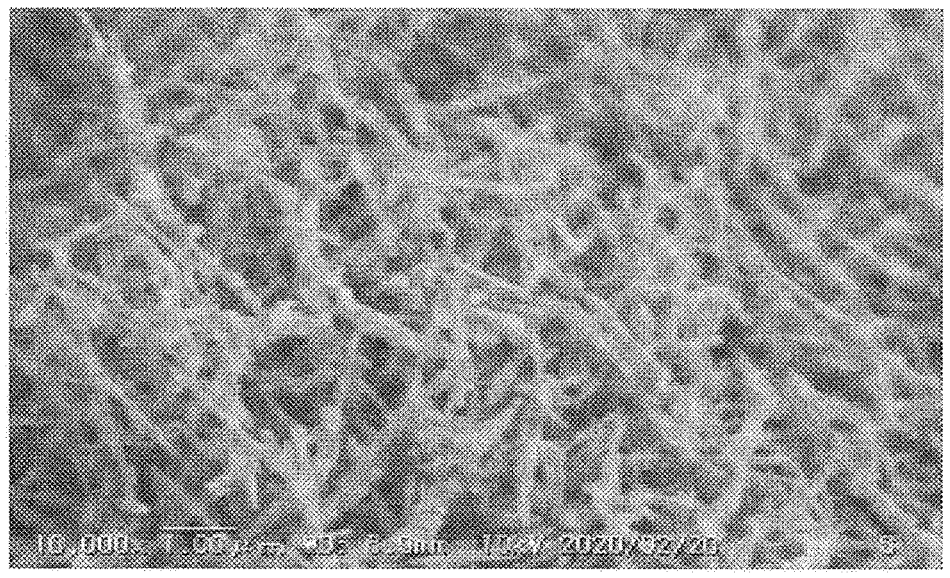
FIG. 1 shows a scanning electron micrograph of the needle-shaped metal oxide used in Examples 1 and 2.

A certain embodiment of the present invention includes a zirconia molded body comprising zirconia, a stabilizing agent capable of preventing a phase transformation of zirconia, a sintering aid, and a needle-shaped metal oxide. A zirconia sintered body satisfying both strength and workability can be obtained with the use of the zirconia molded body. The following first describes a zirconia sintered body as an embodiment of the present invention. The present invention relates to a zirconia sintered body comprising zirconia, a stabilizing agent capable of preventing a phase transformation of zirconia (hereinafter, also referred to as "stabilizing agent"), a sintering aid, and a needle-shaped metal oxide. The descriptions below are not intended to limit the present invention. By "zirconia sintered body", it means, for example, a state after zirconia particles (powder) have sintered. The zirconia sintered body has a relative density of preferably 99.5% or more. The relative density can be calculated as a ratio of the actual density, measured by the Archimedes method, with respect to the theoretical density. By "relative density", it means a value obtained by theoretically dividing density d1 by density d2, where d1 is the density of a sintered body after high-temperature sintering of a molded body prepared by filling granules into a specific mold, and pressing the granules into a specific shape, and d2 is the density of zirconia (with no internal voids). In the present specification, the upper limits and lower limits of numeric ranges (for example, ranges of contents of components, ranges of various elements (such as average fiber diameter, average fiber length, and aspect ratio), and ranges of physical properties (such as three-point flexural strength, Vickers hardness, Mohs hardness, and fracture toughness value)) can be appropriately combined.

[Zirconia Sintered Body]

The average crystal grain size of a zirconia sintered body of the present invention is not particularly limited. In view of satisfying both workability and strength, a zirconia sintered body of the present invention has an average crystal grain size of preferably 1 μm to 10 μm. Workability decreases when the average crystal grain size of the zirconia sintered body is less than 1 μm. The strength decreases when the average crystal grain size of the zirconia sintered body is 10 μm or more. For considerations such as providing a zirconia sintered body satisfying both strength and workability, the average crystal grain size of the zirconia sintered body is preferably 1 μm or more, more preferably 1.5 μm or more, even more preferably 2 μm or more. The average crystal grain size of the zirconia sintered body is preferably 10 μm or less, more preferably 8 μm or less, even more preferably 6 μm or less. The average crystal grain size of the zirconia sintered body can be determined by taking an image of a zirconia sintered body surface with a scanning electron microscope (SEM), and finding the mean value of the diameters of corresponding circles of arbitrarily selected 100 particles (the diameters of true circles having the same area) observed in the captured image.

A zirconia sintered body of the present invention comprises a stabilizing agent. Examples of the stabilizing agent include oxides such as calcium oxide (CaO), magnesium oxide (MgO), yttria ($Y_2O_3$), cerium oxide ($CeO_2$), scandium oxide ($Sc_2O_3$), lanthanum oxide ($La_2O_3$), erbium oxide ($Er_2O_3$), praseodymium oxide ($Pr_6O_{11}$), samarium oxide ($Sm_2O_3$), europium oxide ($Eu_2O_3$), and thulium oxide ($Tm_2O_3$). Yttria is preferred in view of strength and translucency. The content of the stabilizing agent is preferably 0.1 to 18 mol %, more preferably 1 to 15 mol %, even more preferably 2 to 10 mol %. The content of stabilizing agent means the fraction of the number of moles of stabilizing agent (mol %) with respect to the total number of moles of zirconia and stabilizing agent. The content of the stabilizing agent in the zirconia sintered body can be measured by a method, for example, such as inductively coupled plasma (ICP) emission spectral analysis or X-ray fluorescence analysis.

A certain preferred embodiment may be, for example, a zirconia sintered body in which the stabilizing agent comprises yttria, and the content of the yttria is 2.5 to 10 mol %. When the yttria content in the zirconia sintered body is less than 2.5 mol %, the crystalline phase assumes a monoclinic crystal system, and it is not possible to obtain a dense sintered body. The strength decreases when the yttria content in the zirconia sintered body is more than 10 mol %. For considerations such as providing a dense zirconia sintered body having excellent strength, the yttria content in the zirconia sintered body is preferably 2.5 mol % or more. In view of providing excellent translucency, the yttria content in the zirconia sintered body is more preferably 3.5 mol % or more, even more preferably 4.5 mol % or more. The yttria content in the zirconia sintered body is preferably 10 mol % or less, more preferably 8.5 mol % or less. In view of providing excellent strength, the yttria content in the zirconia sintered body is even more preferably 7.0 mol % or less. In embodiments placing greater emphasis on strength, the yttria content in the zirconia sintered body may be 6.5 mol % or less. The yttria content in the zirconia sintered body means the fraction of the number of moles of yttria (mol %) with respect to the total number of moles of zirconia and yttria.

A zirconia sintered body of the present invention comprises a sintering aid. Examples of the sintering aid include niobium pentoxide ($Nb_2O_5$), and tantalum pentoxide ($Ta_2O_5$). Niobium pentoxide is preferred in view of satisfying both strength and workability when combined with the stabilizing agent and the needle-shaped metal oxide. A certain preferred embodiment may be, for example, a zirconia sintered body in which the sintering aid comprises niobium pentoxide, and the content of the niobium pentoxide is 5 to 15 parts by mass with respect to total 100 parts by mass of zirconia and stabilizing agent. Workability decreases when the niobium pentoxide content in the zirconia sintered body is less than 5 parts by mass with respect to total 100 parts by mass of zirconia and stabilizing agent. When the niobium pentoxide content in the zirconia sintered body is more than 15 parts by mass with respect to total 100 parts by mass of zirconia and stabilizing agent, the crystalline phase assumes a monoclinic crystal system, and it is not possible to obtain a dense sintered body. For considerations such as obtaining a dense zirconia sintered body having excellent workability, the niobium pentoxide content in the zirconia sintered body is preferably 5 parts or more by mass, more preferably 6.5 parts or more by mass, even more preferably 8 parts or more by mass. The niobium pentoxide content in the zirconia sintered body is preferably 15 parts or less by mass, more preferably 13.5 parts or less by mass, even more preferably 12 parts or less by mass.

A zirconia sintered body of the present invention comprises a needle-shaped metal oxide. By comprising a needle-shaped metal oxide, the zirconia sintered body can have improved strength while maintaining workability as a sintered body when combined with the stabilizing agent and the sintering aid (preferably, niobium pentoxide). The type of needle-shaped metal oxide is not particularly limited, and one needle-shaped metal oxide, or two or more needle-shaped metal oxides may be used. The needle-shaped metal oxide has a structure such as that shown in FIG. 1. In the present invention, the aspect ratio is the ratio d:D of short axis (d) to long axis (D). In the following, the long axis (D) and short axis (d) of the needle-shaped metal oxide are the average fiber length and the average fiber diameter, respectively. The average fiber length and average fiber diameter can be calculated from a captured SEM image using an image analyzer. Alternatively, a laser diffraction particle size distribution analyzer may be used for the calculations of average fiber length and average fiber diameter.

The aspect ratio of the needle-shaped metal oxide (average fiber diameter:average fiber length) is not particularly limited. However, the aspect ratio is preferably 1:3 or more, more preferably 1:5 or more, even more preferably 1:10 or more in view of the ability to more greatly improve strength while maintaining workability as a sintered body when combined with the stabilizing agent and the sintering aid (preferably, niobium pentoxide). The aspect ratio of the needle-shaped metal oxide is preferably 1:55 or less, more preferably 1:45 or less, even more preferably 1:35 or less in view of the ability to more greatly improve strength while maintaining workability as a sintered body when combined with the stabilizing agent and the sintering aid (preferably, niobium pentoxide).

The average fiber length of the needle-shaped metal oxide is preferably 0.5 μm or more, more preferably 0.75 μm or more, even more preferably 1 μm in view of the ability to more greatly improve strength while maintaining workability as a sintered body when combined with the stabilizing agent and the sintering aid (preferably, niobium pentoxide). The average fiber length of the needle-shaped metal oxide is preferably 15 μm or less, more preferably 13.5 μm or less, even more preferably 12 μm or less in view of the ability to more greatly improve strength while maintaining workability as a sintered body when combined with the stabilizing agent and the sintering aid (preferably, niobium pentoxide).

The average fiber diameter of the needle-shaped metal oxide is preferably 0.01 μm or more, more preferably 0.03 μm or more, even more preferably 0.05 μm in view of the ability to more greatly improve strength while maintaining workability as a sintered body when combined with the stabilizing agent and the sintering aid (preferably, niobium pentoxide). The average fiber diameter of the needle-shaped metal oxide is preferably 3 μm or less, more preferably 2 μm or less, even more preferably 1 μm or less in view of the ability to more greatly improve strength while maintaining workability as a sintered body when combined with the stabilizing agent and the sintering aid (preferably, niobium pentoxide).

The needle-shaped metal oxide is not particularly limited, as long as it is an inorganic metal oxide having a needle-shaped structure. Examples include needle-shaped metal oxides of Al, Si, Y, Ti, Zr, and Sn. The needle-shaped metal oxide may comprise one metallic element alone, or may comprise two or more metallic elements. For example, the needle-shaped metal oxide may be a composite oxide containing two or more of the foregoing metallic elements. A zirconia sintered body of the present invention may use the needle-shaped metal oxide with a metal oxide of a shape other than a needle shape. For considerations such as enhancement of the effectiveness of the present invention, the constituent metallic elements of the needle-shaped metal oxide are preferably Al, Si, Ti, and Sn, more preferably Al and Ti, even more preferably Ti. Examples of the needle-shaped metal oxide include $TiO_2$ and $Al_2O_3$. The needle-shaped metal oxide may be a commercially available product. Examples of such commercially available products include needle-shaped titanium oxides such as the FTL series (for example, FTL-100, FTL-200, FTL-300) manufactured by Ishihara Sangyo Kaisha, Ltd., and needle-shaped alumina fillers such as Cerasur and the BMI series.

The content of the needle-shaped metal oxide in the zirconia sintered body is not particularly limited, and may be appropriately adjusted according to factors such as the type of needle-shaped metal oxide. In view of strength, the content of needle-shaped metal oxide is preferably more than 0 part by mass, more preferably 0.3 parts or more by mass, even more preferably 0.5 parts or more by mass with respect to total 100 parts by mass of zirconia and stabilizing agent. The content of the needle-shaped metal oxide in the zirconia sintered body is preferably 10 parts or less by mass, more preferably 6 parts or less by mass, even more preferably 3 parts or less by mass with respect to total 100 parts by mass of zirconia and stabilizing agent. The strength can improve when the content of the needle-shaped metal oxide has these lower limits and upper limits.

A zirconia sintered body of the present invention may comprise a fluorescent agent. The zirconia sintered body has fluorescence by comprising a fluorescent agent. The fluorescent agent is not particularly limited, and a fluorescent agent with the ability to emit fluorescence in response to light of given wavelengths can be used alone, or two or more of such fluorescent agents may be used. Examples of such fluorescent agents include those containing metallic elements. Examples of the metallic elements include Ga, Bi, Ce, Nd, Sm, Eu, Gd, Tb, Dy, and Tm. The fluorescent agent may contain one of such metallic elements alone, or may contain two or more of such metallic elements. For considerations such as enhancement of the effectiveness of the present invention, preferred among these metallic elements are Ga, Bi, Eu, Gd, and Tm, more preferably Bi and Eu. Examples of the fluorescent agent used when producing a zirconia sintered body of the present invention include oxides, hydroxides, acetates, and nitrates of the metallic elements above. The fluorescent agent may be, for example, $Y_2SiO_5$:Ce, $Y_2SiO_5$:Tb, $(Y,Gd,Eu)BO_3$, yttria:Eu, YAG:Ce, $ZnGa_2O_4$:Zn, or $BaMgAl_{10}O_{17}$:Eu.

The content of the fluorescent agent in the zirconia sintered body is not particularly limited, and can be appropriately adjusted according to factors such as the type of fluorescent agent, and intended use of the zirconia sintered body. In view of considerations such as suitability for use as a dental prosthesis, the content of fluorescent agent is preferably 0.001 mass % or more, more preferably 0.005 mass % or more, even more preferably 0.01 mass % or more in terms of an oxide of a metallic element contained in the fluorescent agent, with respect to the mass of the zirconia contained in the zirconia sintered body. The content of the fluorescent agent in the zirconia sintered body is preferably 1 mass % or less, more preferably 0.5 mass % or less, even more preferably 0.1 mass % or less. With these lower limits of fluorescent agent content, the fluorescence can be comparable to that of human natural teeth. With the foregoing upper limits of fluorescent agent content, it is possible to reduce a decrease in translucency or strength.

A zirconia sintered body of the present invention may comprise a colorant. By comprising a colorant, the zirconia sintered body becomes a colored zirconia sintered body. The type of colorant is not particularly limited, and may be a known pigment commonly used to color ceramics, or a known dental liquid colorant. For example, the colorant may be one containing a metallic element. Specific examples include oxides, composite oxides, and salts containing metallic elements such as iron, vanadium, praseodymium, erbium, chromium, nickel, and manganese. It is also possible to use a commercially available colorant. Examples of commercially available products include the Colour Liquid Prettau® manufactured by Zirkonzahn (Italy). The zirconia sintered body may comprise one colorant, or two or more colorants.

The colorant content in the zirconia sintered body is not particularly limited, and may be appropriately adjusted according to factors such as the type of colorant, and intended use of the zirconia sintered body. In view of considerations such as suitability for use as a dental prosthesis, the colorant content is preferably 0.001 mass % or more, more preferably 0.005 mass % or more, even more preferably 0.01 mass % or more in terms of an oxide of a metallic element contained in the colorant, with respect to the mass of the zirconia contained in the zirconia sintered body. The colorant content in the zirconia sintered body is preferably 5 mass % or less, more preferably 1 mass % or less, even more preferably 0.5 mass % or less. The colorant content may be 0.1 mass % or less, or 0.05 mass % or less.

A zirconia sintered body of the present invention may comprise a translucency adjuster. Specific examples of the translucency adjuster include aluminum oxide, titanium oxide, silicon dioxide, zircon, lithium silicate, and lithium disilicate. However, the translucency adjuster excludes metal oxides having a needle-shaped structure. The zirconia sintered body may comprise one translucency adjuster, or two or more translucency adjusters.

The content of the translucency adjuster in the zirconia sintered body is not particularly limited, and may be appropriately adjusted according to factors such as the type of translucency adjuster, and intended use of the zirconia sintered body. In view of considerations such as suitability for use as a dental prosthesis, the content of translucency adjuster is preferably 0.1 mass % or less with respect to the mass of the zirconia contained in the zirconia sintered body.

A zirconia sintered body of the present invention is obtained by sintering a molded body of a zirconia powder.

The average primary particle diameter of zirconia particles contained in the zirconia powder is not particularly limited. In view of the workability and strength of the sintered body, the average primary particle diameter of zirconia particles is preferably 0.07 μm to 0.25 μm. The workability of the sintered body decreases when the average primary particle diameter of zirconia particles is less than 0.07 μm. The strength of the sintered body decreases when the average primary particle diameter of zirconia particles is more than 0.25 μm. For considerations such as obtaining a zirconia sintered body satisfying both workability and strength in the sintered body, the average primary particle diameter of zirconia particles is preferably 0.07 μm or more, more preferably 0.1 μm or more. The primary particle diameter of zirconia particles is preferably 0.25 μm or less, more preferably 0.2 μm or less. The average primary particle diameter of zirconia particles can be measured using a laser diffraction scattering method. As a specific example of a laser diffraction scattering method, the average primary particle diameter of zirconia particles can be measured by volume using a laser diffraction particle size distribution analyzer (SALD-2300, manufactured by Shimadzu Corporation) with a 0.2% sodium hexametaphosphate aqueous solution used as a dispersion medium.

The method used to prepare zirconia particles in the present invention is not particularly limited. It is possible to employ a method, for example, such as the breakdown process, in which coarse particles are pulverized into a fine powder, and the building-up process, which synthesizes particles through nucleation and growth from atoms or ions. The building-up process is preferred to obtain high-purity fine zirconia particles.

The breakdown process can be performed by using, for example, a ball mill or a bead mill for pulverization. Here, it is preferable to use a microsize pulverization medium, for example, a pulverization medium of 100 μm or less. Preferably, the zirconia particles are classified after pulverization.

Examples of the building-up process include:

vapor-phase pyrolysis that precipitates oxides through pyrolysis while vaporizing high-vapor-pressure oxoacid salts or organometallic compounds of metal ions;

gas phase reaction whereby a gas-phase chemical reaction between a gas of high-vapor-pressure metal compounds and a reactant gas is performed for synthesis;

evaporative concentration that heats and vaporizes raw materials, and condenses the vapor into fine particles through rapid cooling in an inert gas of a predetermined pressure;

the melt process that forms a powder by cooling and solidifying small droplets of a melt;

solvent evaporation that evaporates a solvent to increase the solution concentration and create a supersaturated state for precipitation; and the precipitation process whereby poorly soluble compounds such as oxides and hydroxides are precipitated through the process of nucleation and growth by bringing the solute concentration into a supersaturated state by a reaction or hydrolysis with a precipitating agent.

The precipitation process can be classified into different categories, some of which include:

homogenous precipitation in which a precipitating agent is generated in a solution through chemical reaction to eliminate local concentration nonuniformity of precipitating agent;

coprecipitation in which a precipitating agent is added to simultaneously precipitate more than one metal ion present in the solution;

hydrolysis that forms oxides or hydroxides through hydrolysis from a metal salt solution or an alcohol solution such as an alcohol solution of metal alkoxides; and solvothermal synthesis that forms oxides or hydroxides from a high-temperature high-pressure fluid.

The solvothermal synthesis can be further divided into, for example, hydrothermal synthesis that uses water as solvent, and supercritical synthesis in which a supercritical fluid such as water or carbon dioxide is used as solvent.

It is preferable to increase the precipitation rate to obtain finer zirconia particles, irrespective of which building-up process is used. It is also preferable to classify the zirconia particles obtained.

Examples of the zirconium source in the building-up process include nitrates, acetates, chlorides, and alkoxides, specifically, zirconium oxychloride, zirconium acetate, and zirconyl nitrate.

Examples of the yttrium source include nitrates, acetates, chlorides, and alkoxides, specifically, yttrium chloride, yttrium acetate, and yttrium nitrate.

A zirconia sintered body of the present invention is obtained by sintering a molded body or pre-sintered body of the zirconia powder. The zirconia powder can be obtained by drying a slurry containing zirconia particles. However, the drying method is not particularly limited, and may be, for example, spray drying, supercritical drying, freeze drying, hot-air drying, or vacuum drying. For considerations such as the ability to obtain a denser zirconia sintered body by reducing particle aggregation during drying, preferred is any of spray drying, supercritical drying, and freeze drying, more preferably spray drying or supercritical drying, even more preferably spray drying.

The dispersion medium of the zirconia particle-containing slurry subjected to drying is not particularly limited. In view of achieving uniform dispersion, the dispersion medium may be, for example, water or an organic solvent. In view of environmental stress, water is preferred.

A zirconia sintered body of the present invention is obtained by sintering a zirconia molded body. The zirconia molded body may be produced by press forming a zirconia powder. The specific method of press forming is not particularly limited, and a known pressing machine may be used. Specific examples of press forming methods include uniaxial pressing. In order to increase the density of the zirconia molded body obtained, it is preferable that uniaxial pressing be followed by a CIP (Cold Isostatic Pressing) process.

A zirconia pre-sintered body of the present invention is obtained by pre-sintering a zirconia molded body. A preferred method of production of the zirconia pre-sintered body is, for example, a production method that comprises the step of pre-sintering a zirconia molded body of the present invention at 200° C. or more and less than 1,200° C. In view of considerations such as easiness of obtaining the desired zirconia pre-sintered body, the pre-sintering temperature is preferably 200° C. or more, more preferably 300° C. or more, even more preferably 500° C. or more. The pre-sintering temperature is preferably 1,200° C. or less, more preferably 1,150° C. or less, even more preferably 1,100° C. or less. Here, a zirconia pre-sintered body means, for example, a semi-sintered body that has formed a block while the zirconia particles (powder) were not fully sintered.

The rate of temperature increase in pre-sintering a zirconia molded body of the present invention is not particularly limited. However, the rate of temperature increase is preferably 0.1° C./min or more, more preferably 0.2° C./min or more, even more preferably 0.5° C./min or more. The rate of temperature increase is preferably 50° C./min or less, more preferably 30° C./min or less, even more preferably 20° C./min or less. The productivity improves when the rate of temperature increase has the foregoing lower limits. With the foregoing upper limits of rate of temperature increase, the volume difference between the inside and outside of the zirconia molded body can be reduced, and, when the zirconia molded body contains an organic material, cracking or breakage can be prevented by reducing the abrupt decomposition of the organic material.

Aside from being a sintered body (zirconia primary sintered body) obtained by sintering a zirconia molded body or zirconia pre-sintered body of the present invention under ordinary pressure or under no applied pressure, a zirconia sintered body of the present invention may be sintered by HIP (Hot Isostatic Pressing). The zirconia primary sintered body may be subjected to HIP.

In a zirconia sintered body of the present invention, the sintering temperature is not particularly limited in sintering the zirconia molded body or in sintering the zirconia pre-sintered body. However, for considerations such as the ability to obtain a sintered body having good workability and strength, the sintering temperature is preferably 1,350° C. or more, more preferably 1,450° C. or more, even more preferably 1,500° C. or more. The sintering temperature is preferably 1,800° C. or less, more preferably 1,700° C. or less, even more preferably 1,650° C. or less.

In a zirconia sintered body of the present invention, the rate of temperature increase is not particularly limited in sintering the zirconia molded body or in sintering the zirconia pre-sintered body. However, the rate of temperature increase is preferably or more, more preferably 0.2° C./min or more, even more preferably 0.5° C./min or more. The rate of temperature increase is preferably 50° C./min or less, more preferably 30° C./min or less, even more preferably 20° C./min or less. The productivity improves when the rate of temperature increase has the foregoing lower limits. With the foregoing upper limits of rate of temperature increase, the volume difference between the inside and outside of the zirconia molded body or zirconia pre-sintered body can be reduced, and, when the zirconia molded body contains an organic material, cracking or breakage can be reduced by reducing the abrupt decomposition of the organic material.

In a zirconia sintered body of the present invention, the sintering time is not particularly limited in sintering the zirconia molded body or in sintering the zirconia pre-sintered body. However, for considerations such as the ability to efficiently and stably produce the desired zirconia sintered body with good productivity, the sintering time is preferably 5 minutes or more, more preferably 8 minutes or more, even more preferably 10 minutes or more. The sintering time is preferably 10 hours or less, more preferably 7 hours or less, even more preferably 5 hours or less.

In a zirconia sintered body of the present invention, the HIP temperature is not particularly limited in HIP of the zirconia molded body, HIP of the zirconia pre-sintered body, or HIP of the zirconia primary sintered body. However, for considerations such as the ability to obtain a dense sintered body having high strength, the HIP temperature is preferably 1,000° C. or more, more preferably 1,200° C. or more, even more preferably 1,300° C. or more. The HIP temperature is preferably 1,700° C. or less, more preferably 1,650° C. or less, even more preferably 1,600° C. or less.

In a zirconia sintered body of the present invention, the rate of temperature increase is not particularly limited in HIP of the zirconia molded body, HIP of the zirconia pre-sintered body, or HIP of the zirconia primary sintered body. However, the rate of temperature increase is preferably 0.1° C./min or more, more preferably 0.2° C./min or more, even more preferably 0.5° C./min or more. The rate of temperature increase is preferably 50° C./min or less, more preferably 30° C./min or less, even more preferably or less. The productivity improves when the rate of temperature increase has the foregoing lower limits. With the foregoing upper limits of rate of temperature increase, the volume difference between the inside and outside of the zirconia molded body, zirconia pre-sintered body, or zirconia primary sintered body can be reduced, and, when the zirconia molded body contains an organic material, cracking or breakage can be reduced by reducing the abrupt decomposition of the organic material.

In a zirconia sintered body of the present invention, the HIP pressure is not particularly limited in HIP of the zirconia molded body, HIP of the zirconia pre-sintered body, or HIP of the zirconia primary sintered body. However, for consideration such as the ability to obtain a dense sintered body having high strength, the HIP pressure is preferably 100 MPa or more, more preferably 125 MPa or more, even more preferably 130 MPa or more. The HIP pressure is preferably 200 MPa or less, more preferably 185 MPa or less, even more preferably 170 MPa or less.

In a zirconia sintered body of the present invention, the HIP time is not particularly limited in HIP of the zirconia molded body, HIP of the zirconia pre-sintered body, or HIP of the zirconia primary sintered body. However, for consideration such as the ability to obtain a dense sintered body having high strength, the HIP time is preferably 5 minutes or more, more preferably 10 minutes or more, even more preferably 30 minutes or more. The HIP time is preferably 10 hours or less, more preferably 6 hours or less, even more preferably 3 hours or less.

In a zirconia sintered body of the present invention, the pressure medium is not particularly limited in HIP of the zirconia molded body, HIP of the zirconia pre-sintered body, or HIP of the zirconia primary sintered body. However, in view of having low impact on zirconia, the pressure medium is at least one selected from the group consisting of oxygen and an inert gas (for example, nitrogen, argon).

A zirconia sintered body of the present invention excels in strength. A zirconia sintered body of the present invention has a three-point flexural strength of preferably 500 MPa or more, more preferably 530 MPa or more, even more preferably 540 MPa or more. With a zirconia sintered body of the present invention having such a three-point flexural strength, it is possible to reduce defects such as fracture in the oral cavity when used as a dental prosthesis, for example. The upper limit of three-point flexural strength is not particularly limited, and the three-point flexural strength may be, for example, 2,000 MPa or less, or 1,500 MPa or less. The three-point flexural strength of the zirconia sintered body can be measured in compliance with ISO 6872:2015.

It is preferable that a zirconia sintered body of the present invention have high translucency. The translucency can be evaluated using $\Delta L^*(W-B)$. Specifically, concerning translucency, a zirconia sintered body of the present invention has a $\Delta L^*(W-B)$ of 6 or more, more preferably 8 or more, even more preferably 10 or more at 14 mm diameter and 1.2 mm thickness.

Here, $\Delta L^*(W-B)$ means the difference between a lightness (L*) against a white background and a lightness (L*) against a black background. Specifically, it means the difference between an L* value against a white background (JIS Z 8781-4:2013 Color Measurements—Part 4: CIE 1976 L*a*b* color space) and an L* value against a black background. A white background means the white part of the hiding-power test paper described in JIS K 5600-4-1:1999, Part 4, Section 1, and a black background means the black part of the hiding-power test paper. A zirconia sintered body of high translucency can be obtained when the $\Delta L^*(W-B)$ is confined within the foregoing ranges. The upper limit of $\Delta L^*(W-B)$ is preferably, for example, 30 or less, though it is not particularly limited. In view of aesthetics, the upper limit of $\Delta L^*(W-B)$ may be 25 or less. The $\Delta L^*(W-B)$ of the zirconia sintered body at 14 mm diameter and 1.2 mm thickness can be measured using a spectrophotometer. For example, measurements were made after applying a contact liquid to a specimen surface, using a dental colorimeter (Crystaleye CE100-CE/JP, a 7-band LED light source, and analysis software Crystaleye, manufactured by Olympus Corporation). The contact liquid may be, for example, one having a refractive index nD of 1.60 as measured at 589 nm wavelength (sodium D-line).

A zirconia sintered body of the present invention excels in workability. The workability of a zirconia sintered body of the present invention can be determined by, for example, the hardness. The method of hardness measurement of a zirconia sintered body according to the present invention is not particularly limited, and the hardness can be measured with, for example, a Mohs hardness meter, in a scale of 1 to 10. A zirconia sintered body of the present invention has a Mohs hardness of preferably 9.5 or less, more preferably 8.5 or less. By having such a Mohs hardness, a zirconia sintered body of the present invention can exhibit good workability. In view of reducing the breakage of dental restorations in the oral cavity, the Mohs hardness is preferably 3.5 or more, more preferably 4.5 or more.

A zirconia sintered body of the present invention excels in workability. The workability of a zirconia sintered body of the present invention is determined by, for example, the Vickers hardness. The Vickers hardness of a zirconia sintered body of the present invention can be measured using a Vickers hardness meter. A zirconia sintered body of the present invention has a Vickers hardness of preferably 1,200 HV or less, more preferably 1,050 HV or less, even more preferably 950 HV or less. By having such a Vickers hardness, a zirconia sintered body of the present invention exhibits good workability. In view of reducing the breakage of dental restorations in the oral cavity, the Vickers hardness is preferably 150 HV or more, more preferably 300 HV or more, even more preferably 500 HV or more. The Vickers hardness of the zirconia sintered body can be measured in compliance with JIS Z 2244:2009. In the measurement of Vickers hardness, for example, an HV value can be calculated under an applied load of 5 kgf for 30 seconds, using a micro/macro Vickers hardness tester (FALCON 509FA, manufactured by Innovatest Japan under this trade name). For example, a mean value may be calculated for n=10.

A zirconia sintered body of the present invention excels in workability. The workability of a zirconia sintered body of the present invention is also determined by, for example, the fracture toughness value. The method of measurement of the fracture toughness value of a zirconia sintered body according to the present invention is not particularly limited, and the fracture toughness value can be measured by, for example, the indentation-fracture method (IF method). A zirconia sintered body of the present invention has a fracture toughness value of preferably 5 $MPa \cdot m^{1/2}$ or more, more preferably 6 $MPa \cdot m^{1/2}$ or more, even more preferably 7 $MPa \cdot m^{1/2}$ or more. By having such a fracture toughness value, a zirconia sintered body of the present invention exhibits even more desirable workability. The upper limit of fracture toughness value is not particularly limited. The fracture toughness value may be, for example, 10 $MPa \cdot m^{1/2}$ or more, or 15 $MPa \cdot m^{1/2}$ or more. The fracture toughness value of the zirconia sintered body can be measured in compliance with JIS R 1607:2015.

A zirconia sintered body of the present invention can be worked into a crown shape using a computer-aided dental design and manufacturing unit. For processing of dental restorations with a computer-aided dental design and manufacturing unit, it is possible to select, for example, dry milling, wet milling, or wet grinding. In view of work efficiency, it is preferable to use wet grinding for a zirconia sintered body of the present invention. Any commercially available computer-aided dental design and manufacturing unit can be used for the processing of a zirconia sintered body of the present invention, including, for example, CEREC MC XL (manufactured by Dentsply Sirona), CEREC Primemill (manufactured by Dentsply Sirona), and DWX-42W (manufactured by Roland DG Corporation).

[Uses of Zirconia Sintered Body]

A zirconia sintered body of the present invention is not limited to particular shapes, and may have a shape of, for example, a disc or a prism. Because of excellent workability, various shapes can be selected for different uses, offering good crown-shape selectivity. A zirconia sintered body of the present invention is not limited to particular uses. However, a zirconia sintered body of the present invention is particularly suited as, for example, a dental material, such as a dental prosthesis, because a zirconia sintered body of the present invention has high crown-shape selectivity, and can be machined while maintaining high in strength.

EXAMPLES

The present invention is described below in greater detail using Examples and Comparative Examples. It is to be noted, however, that the present invention is not limited by the following. The oxide materials, and the methods used for the measurement of various physical properties in Examples and Comparative Examples are as follows.

[Needle-Shaped Metal Oxide]

Needle-shaped metal oxide T1: needle-shaped $TiO_2$, average fiber length: 1.68 μm, average fiber diameter: 0.13 μm, aspect ratio (average fiber diameter:average fiber length)=1:13

Needle-shaped metal oxide T2: needle-shaped $TiO_2$, average fiber length: 10.47 μm, average fiber diameter: 0.5 μm, aspect ratio (average fiber diameter:average fiber length)=1:21

Needle-shaped metal oxide T3: needle-shaped $Al_2O_3$, average fiber length: 2.5 μm, average fiber diameter: 0.1 μm, aspect ratio (average fiber diameter:average fiber length)=1:25

[Metal Oxide Other than Needle-Shaped Metal Oxides]

Granular metal oxide X1: granular $TiO_2$, average particle diameter: 0.3 to 1.0 μm

[Average Crystal Grain Size]

The average crystal grain size of zirconia sintered bodies was determined by capturing an image of a surface of the zirconia sintered body obtained in each Example and Comparative Example, using a scanning electron microscope (VE-9800 manufactured by Keyence under this trade name), and finding the mean value of the diameters of corresponding circles of arbitrarily selected 100 particles (the diameters of true circles having the same area) observed in the captured image.

[Translucency ΔL*(W–B)]

The translucency ΔL*(W–B) was calculated using L* values of chromaticity (color space) according to the L*a*b*color system (JIS Z 8781-4: 2013), using a dental colorimeter (Crystaleye CE100-CE/JP, a 7-band LED light source, manufactured by Olympus Corporation) with analysis software Crystaleye (manufactured by Olympus Corporation) (n=1). A zirconia sintered body of 14 mm diameter and 1.2 mm thickness was used for the measurement. The L* value measured for a specimen of the sintered body against a white background was used as a first L* value, and the same specimen used for the measurement of first L* value was measured for a second L* value against a black background. The second L* value was then subtracted from the first L* value to derive a value indicative of translucency. A contact liquid having a refractive index nD of 1.60 was applied to the specimen's measurement surface. Here, the white background means the white part of the hiding-power test paper described in JIS K 5600-4-1:1999, Part 4, Section 1, and the black background means the black part of the hiding-power test paper.

[Mohs Hardness]

The Mohs hardness was measured using a Mohs hardness meter (manufactured by Tokyo-Science Co., Ltd.).

[Vickers Hardness]

The Vickers hardness was measured under an applied load of 5 kgf for 30 seconds in compliance with JIS Z 2244: 2009, using a micro/macro Vickers hardness tester (FALCON 509FA, manufactured by Innovatest Japan under this trade name).

[Fracture Toughness Value]

The fracture toughness value was measured in compliance with JIS R 1607: 2015, using a micro/macro Vickers hardness tester (FALCON 509FA, manufactured by Innovatest Japan under this trade name).

[Three-Point Flexural Strength]

The three-point flexural strength was measured for a zirconia sintered body (14 mm in width×14 mm in length× 14 mm in thickness) in compliance with ISO 6872: 2015 using a universal testing machine AGS-X (manufactured by Shimadzu Corporation) at a span length of 30 mm and a crosshead speed of 0.5 mm/min (a mean value for n=3).

[Grinding Volume]

The grinding volume was measured for each zirconia sintered body by measuring the amount of grinding in a sintered body block (14 mm in length×14 mm in width×14 mm in thickness) before the processing device was forced to automatically shut down due to failure after the grinding was started. The sintered body block was processed by wet grinding, using a computer-aided dental design and manufacturing unit DWX-42W (manufactured by Roland DG Corporation). The processing device used a milling bur ZGB2-125D for coarse grinding (manufactured by Roland DG Corporation), and a milling bur ZGB2-50D for finishing (manufactured by Roland DG Corporation).

[Grinding Time]

The grinding time is a time period from the start of grinding to the processing device being forced to automatically shut down in response to increased workload due to wearing of the milling bur grinding the block in the measurement of grinding volume.

Examples 1 to 5 and Comparative Example 1

Figure 2:
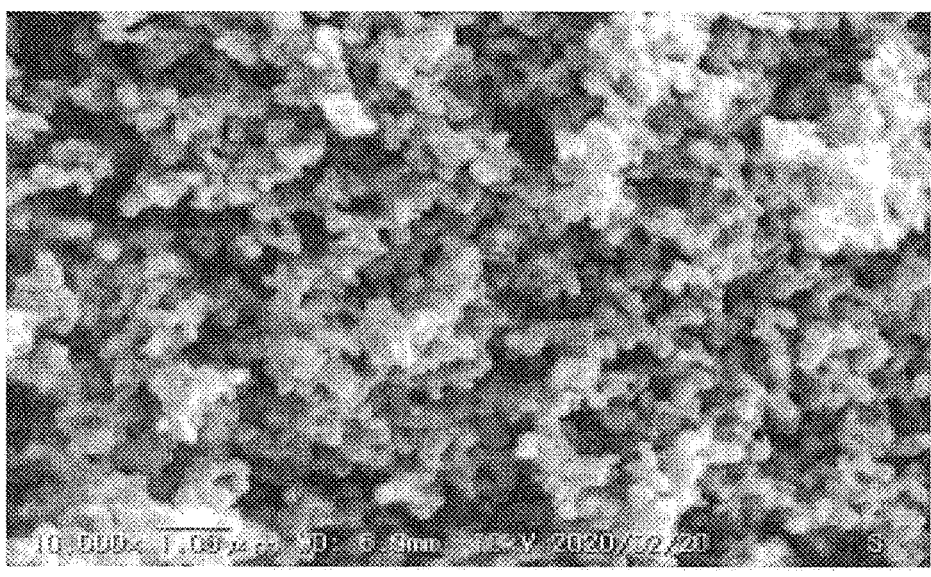
FIG. 2 shows a scanning electron micrograph of the metal oxide used in Comparative Example 1.

A mixture of zirconia, yttria, and niobium pentoxide with a needle-shaped metal oxide or a granular metal oxide was prepared as shown in Table 1. The mixture was added into water to prepare a slurry, and the slurry was mixed and pulverized wet with a ball mill until the zirconia particles had an average primary particle diameter of 0.13 μm. After pulverization, the slurry was dried with a spray dryer to obtain a zirconia powder. The zirconia powder was press formed under a pressure of 300 kg/cm 2, followed by CIP at 1,700 kg/cm 2 to obtain a zirconia molded body, in order to produce a zirconia sintered body measuring 14 mm in diameter and 1.2 mm in thickness, a zirconia sintered body measuring 4 mm in width, 16 mm in length, and 1.2 mm in thickness, and a zirconia sintered body measuring 14 mm in width, 14 mm in length, and 14 mm in thickness. The zirconia molded body was sintered at 1,550° C. for 120 minutes, and subjected to HIP at 1,450° C. for 60 minutes under 150 MPa conditions (used gases Ar:$O_2$=80:20) to prepare zirconia sintered bodies of Examples 1 to 5 and Comparative Example 1. The results are presented in Table 1. FIG. 1 shows an SEM image of the needle-shaped metal oxide T1 used in Examples 1 and 2. FIG. 2 shows an SEM image of the granular metal oxide X1 used in Comparative Example 1.

Comparative Example 2

A mixture of zirconia and yttria was prepared as shown in Table 1. The mixture was added into water to prepare a slurry, and the slurry was mixed and pulverized wet with a ball mill until the zirconia particles had an average primary particle diameter of 0.13 μm. After pulverization, the slurry was dried with a spray dryer to obtain a zirconia powder. The zirconia powder was press formed under a pressure of 300 kg/cm 2, followed by CIP at 1,700 kg/cm 2 to obtain a zirconia molded body, in order to produce a zirconia sintered body measuring 14 mm in diameter and 1.2 mm in thickness, a zirconia sintered body measuring 4 mm in width, 16 mm in length, and 1.2 mm in thickness, and a zirconia sintered body measuring 14 mm in width, 14 mm in length, and 14 mm in thickness. The zirconia molded body was sintered at a sintering temperature of 1,500° C. for 120 minutes to prepare a zirconia sintered body. The results are presented in Table 1.

Comparative Example 3

A zirconia sintered body was prepared using the same method used in Comparative Example 2, except that the zirconia and yttria had a mole ratio of 94.5:5.5, and that the sintering temperature was changed to 1,550° C.

Comparative Example 4

A zirconia sintered body was prepared using the same method used in Comparative Example 2, except that 10 parts by mass of niobium pentoxide was added in Comparative Example 2. The zirconia sintered body of Comparative Example 4 failed to maintain its shape, and collapsed after sintering, and it was not possible to measure strength and other physical properties.

Comparative Example 5

A zirconia sintered body was prepared using the same method used in Comparative Example 3, except that 10 parts by mass of niobium pentoxide was added in Comparative Example 3.

Here is an overview of the translucency ΔL*(W–B) of the zirconia sintered bodies. The translucency ΔL*(W–B) was 7 or higher, and was desirable in all of the Examples and Comparative Examples. Examples 1, 2, and 5, and Comparative Examples 1, 3, and 5 were particularly superior with the ΔL*(W–B) values of 12 or higher.

Here is an overview of the Mohs hardness of the zirconia sintered bodies. The Mohs hardness was 9.5 or less, and was desirable in all of the Examples and Comparative Examples. Examples 1, 2, and 5, and Comparative Examples 1 and 5 were particularly superior with the Mohs hardnesses of 8.5 or less.

Here is an overview of the Vickers hardness of the zirconia sintered bodies. The Vickers hardness was 1,050 HV or less, and was desirable in Examples 1 to 5 and Comparative Examples 1 and 5. Examples 1, 2, and 5, and Comparative Examples 1 and 5 were particularly superior with the Vickers hardnesses of 950 HV or less. Comparative Examples 2 and 3 had Vickers hardnesses of 1,200 HV or more, presumably making the zirconia sintered bodies inferior in terms of workability.

Here is an overview of the fracture toughness value of the zirconia sintered bodies. The fracture toughness value was 5 MPa·m$^{1/2}$ or more, and was desirable in Examples 1 to 5 and Comparative Examples 1 and 5. Examples 1, 2, and 5, and Comparative Examples 1 and 5 were particularly superior with the fracture toughness values of 7 MPa·m$^{1/2}$ or more. Comparative Examples 2 and 3 had fracture toughness values of 5 MPa·m$^{1/2}$ or less, presumably making the zirconia sintered bodies inferior in terms of workability.

Here is an overview of the three-point flexural strength of the zirconia sintered bodies. The three-point flexural strength was 500 MPa or more, and was desirable in Examples 1 to 5 and Comparative Examples 2 and 3. Comparative Examples 1 and 5 had three-point flexural strengths of less than 500 MPa, posing a possibility of fracture in a dental restoration in the oral cavity.

Here is an overview of the grinding volume of the zirconia sintered bodies. Examples 1 to 5 and Comparative Examples 1 and 5 were workable. The workability was particularly superior in Examples 1, 2, and 5, and Comparative Examples 1 and 5. Comparative Examples 2 and 3 were barely workable.

TABLE 1

| Composition | | Ex. 1 | Ex. 2 | Ex. 3 | Ex. 4 | Ex. 5 | Com. Ex. 1 | Com. Ex. 2 | Com. Ex. 3 | Com. Ex. 4 | Com. Ex. 5 |
|---|---|---|---|---|---|---|---|---|---|---|---|
| Composition | $ZrO_2$ [mol %] | 94.5 | 94.5 | 94.5 | 94.5 | 94.5 | 94.5 | 97 | 94.5 | 97 | 94.5 |
| | $Y_2O_3$ [mol %] | 5.5 | 5.5 | 5.5 | 5.5 | 5.5 | 5.5 | 3 | 5.5 | 3 | 5.5 |
| | $Nb_2O_5$ [parts by mass] | 10 | 10 | 10 | 10 | 10 | 10 | — | — | 10 | 10 |
| | Needle-shaped metal oxide T1 [parts by mass] | 2.5 | 5 | — | — | — | — | — | — | — | — |
| | Needle-shaped metal oxide T2 [parts by mass] | — | — | — | — | 2.5 | — | — | — | — | — |

TABLE 1-continued

| | Ex. 1 | Ex. 2 | Ex. 3 | Ex. 4 | Ex. 5 | Com. Ex. 1 | Com. Ex. 2 | Com. Ex. 3 | Com. Ex. 4 | Com. Ex. 5 |
|---|---|---|---|---|---|---|---|---|---|---|
| Granular metal oxide X1 [parts by mass] | — | — | — | — | — | 2.5 | — | — | — | — |
| Needle-shaped metal oxide T3 [parts by mass] | — | — | 0.5 | 1 | — | — | — | — | — | — |
| Average crystal grain size [μm] | 5.2 | 6.0 | 2.0 | 2.5 | 5.3 | 5.4 | 0.5 | 1.3 | — | 5.2 |
| Translucency ΔL*(W-B) [-] | 13 | 13 | 8 | 8 | 12 | 13 | 11 | 16 | — | 13 |
| Mohs hardness [-] | 8.5 | 8.5 | 9.5 | 9.5 | 8.5 | 8.5 | 9.5 | 9.5 | — | 8.5 |
| Vickers hardness [HV] | 897 | 908 | 979 | 989 | 896 | 936 | 1260 | 1260 | — | 897 |
| Fracture toughness value [MPa · m$^{1/2}$] | 8.2 | 7.5 | 6.7 | 6.5 | 8.3 | 7.9 | 4.6 | 2.8 | — | 8.6 |
| Three-point flexural strength [MPa] | 565 | 536 | 665 | 698 | 541 | 480 | 1200 | 750 | — | 292 |
| Grinding volume [cm$^3$] | 18.2 | 18.2 | 0.7 | 0.7 | 17.9 | 26.1 | 0.001 | 0.001 | — | 26.1 |
| Grinding time [min] | 280 | 280 | 11 | 11 | 275 | 402 | 0.01 | 0.01 | — | 402 |

In the table, the content of needle-shaped metal oxide, and the content of granular metal oxide mean the content (parts by mass) with respect to total 100 parts by mass of zirconia ($ZrO_2$) and yttria ($Y_2O_3$).

INDUSTRIAL APPLICABILITY

A zirconia sintered body of the present invention, and a method of production of the zirconia sintered body can be used in a wide range of applications, including, for example, dental products such as dental prostheses; connector components for optical fibers, such as ferrules and sleeves; various tools (for example, grinding balls, grinding tools); various components (for example, screws, bolts, nuts); various sensors; electronics components; and ornaments (for example, wrist bands for watches). For applications as dental materials, the sintered body can be used for, for example, copings, frameworks, crowns, crown bridges, abutments, implants, implant screws, implant fixtures, implant bridges, implant burs, brackets, denture bases, inlays, onlays, orthodontic wires, and laminate veneers.

The invention claimed is:

1. A zirconia sintered body, comprising:
   zirconia,
   a stabilizing agent capable of preventing a phase transformation of the zirconia,
   a sintering aid, which contains niobium pentoxide in a content of 5 to 15 parts by mass with respect to a total 100 parts by mass of the zirconia and the stabilizing agent, and
   a needle-shaped metal oxide.

2. The zirconia sintered body according to claim 1, wherein the stabilizing agent comprises yttria, and a content of the yttria is 2.5 to 10 mol % with respect to a total number of moles of the zirconia and the yttria.

3. The zirconia sintered body according to claim 1, wherein the needle-shaped metal oxide has an aspect ratio d:D of 1:3 to 1:55, where d and D represent average fiber diameter and average fiber length of the needle-shaped metal oxide, respectively.

4. The zirconia sintered body according to claim 1, wherein a content of the needle-shaped metal oxide is more than 0 part by mass and 10 parts or less by mass with respect to the total 100 parts by mass of the zirconia and the stabilizing agent.

5. The zirconia sintered body according to claim 1, which has a Vickers hardness of 1,050 HV or less.

6. The zirconia sintered body according to claim 1, which has a fracture toughness value of 5 MPa·m$^{1/2}$ or more.

7. The zirconia sintered body according to claim 1, which has a three-point flexural strength of 500 MPa or more.

8. The zirconia sintered body according to claim 1, having an average crystal grain size, which is an average of equivalent circle diameters of any 100 particles observed on a surface of the zirconia sintered body, of 1 to 10 μm.

9. The zirconia sintered body according to claim 1, wherein the needle-shaped metal oxide comprises at least one metallic element selected from the group consisting of Al, Si, Y, Ti, Zr, and Sn.

10. The zirconia sintered body according to claim 1, wherein the needle-shaped metal oxide comprises at least one metallic element selected from the group consisting of Al, Si, Ti, and Sn.

11. The zirconia sintered body according to claim 1, wherein the needle-shaped metal oxide comprises at least one metallic element selected from the group consisting of Al and Ti.

12. The zirconia sintered body according to claim 1, wherein the needle-shaped metal oxide comprises $TiO_2$.

* * * * *